United States Patent [19]

Carson et al.

[11] 4,216,150

[45] Aug. 5, 1980

[54] PREPARATION OF PYRROLE-2-ACETATES

[75] Inventors: John R. Carson; Richard J. Carmosin, both of Norristown; Anthony T. Stefanski, Bethlehem, all of Pa.

[73] Assignee: McNeil Lab, Inc., Fort Washington, Pa.

[21] Appl. No.: 951,559

[22] Filed: Oct. 16, 1978

Related U.S. Application Data

[63] Continuation-in-part of Ser. No. 789,310, Apr. 20, 1977, abandoned.

[51] Int. Cl.$^2$ ............................................. C07D 207/32
[52] U.S. Cl. ............................. 260/326.2; 260/326.47
[58] Field of Search ................. 260/326.2, 689, 566 R

[56] References Cited

U.S. PATENT DOCUMENTS

| | | | |
|---|---|---|---|
| 3,393,201 | 7/1968 | Preau | 260/326.2 |
| 3,544,589 | 12/1970 | Orth | 260/326.2 |
| 3,803,169 | 4/1974 | Carson | 260/326.2 |
| 3,957,818 | 5/1976 | Carson | 260/326.2 |
| 3,998,844 | 12/1976 | Carson | 260/326.2 |

OTHER PUBLICATIONS

Mayer et al.; Ang. Chem., vol. 75, pp. 1011–1014, (1963).
Smith; The Chemistry of Open–Chain Organic Nitrogen Compounds, pp. 300–301, (1965.
Reeves; J.A.C.S., vol. 84, p. 3332, (1962).
Theilheimer; Synthetic Methods; vol. 19; p. 80, vol. 15:667.
Layer; Chemical Review, vol. 63, pp. 490–493, 497–498, (1963).

*Primary Examiner*—Mary C. Lee

[57] ABSTRACT

Loweralkyl 1-methylpyrrole-2-acetates are prepared by the recuction of loweralkyl α-imino-1-methylpyrrole-2-acetates using a divalent sulfur reducing agent.

16 Claims, No Drawings

PREPARATION OF PYRROLE-2-ACETATES

CROSS-REFERENCE TO RELATED APPLICATION

This is a continuation-in-part application of our copending application Ser. No. 789,310, filed Apr. 20, 1977, now abandoned.

DESCRIPTION OF THE PREFERRED EMBODIMENT

This invention relates to a novel process of preparing loweralkyl 1-methylpyrrole-2-acetates of the formula:

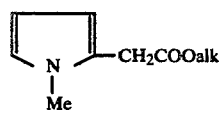

wherein alk is loweralkyl, preferably ethyl.

According to the instant process, an appropriate loweralkyl α-imino-1-methylpyrrole-2-acetate of formula (II), wherein alk is as previously defined and R is a member selected from the group consisting of hydrogen, loweralkyl, cycloalkyl, phenyl and phenyl substituted with from one to three substituents each selected from the group consisting of loweralkyl, loweralkyloxy and halo, is reduced to a corresponding loweralkyl 1-methylpyrrole-2-acetate of formula (I) by the action of a divalent sulfur reducing agent.

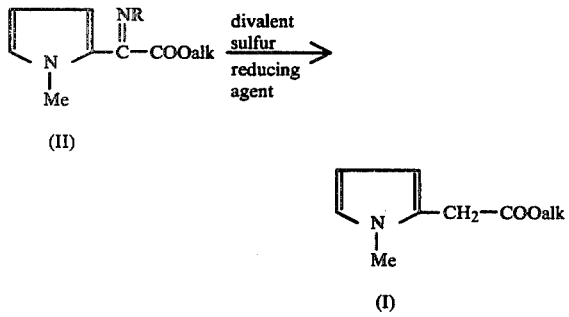

As used herein, "loweralkyl" refers to straight or branch chained alkyls having from 1 to 6 carbons, for example, methyl, ethyl, propyl, isopropyl, butyl, tert-butyl, pentyl, hexyl and the like; "halo" refers to chloro, bromo, fluoro and iodo; and "cyclohexyl" refers to cyclopentyl and cyclohexyl.

Divalent sulfur reducing agents preferred for the foregoing reduction reaction are hydrogen sulfide and an alkali metal hydrogen sulfide, e.g., sodium hydrogen sulfide, and the like. Also suitable are sodium polysulfide and ammonium polysulfide. Most preferred is hydrogen sulfide.

Suitable solvents which may be utilized for the reduction reaction are aromatic hydrocarbons such as, for example, benzene, toluene, xylene and the like; halocarbons such as, for example, methylene dichloride, chloroform and the like; amines such as, for example, pyridine, triethylamine, triethanolamine and the like; lower alkanols, such as, for example, methanol, ethanol, methoxyethanol and the like; and dipolar aprotic organic solvents such as, for example, dimethyl sulfoxide (DMSO), N,N-dimethylformamide (DMF), ethyl acetate, acetonitrile and the like.

The reduction reaction may be performed at reaction temperatures varying from about $-20°$ C. to about $50°$ C. and atmospheric pressure to about 60 p.s.i. pressure may be advantageously employed.

The loweralkyl 1-methylpyrrole-2-acetates of formula (I) have been reported in the literature as being useful intermediates in the preparation of 5-aroyl-pyrrole-2-acetic acid derivatives having anti-inflammatory activity (e.g., see U.S. Pat. Nos. 3,752,826; 3,803,169; 3,846,447; and 3,957,818).

The α-imino-acetate precursors of formula (II) are obtainable by several methods. For example, by reacting a loweralkyl 1-methylpyrrole-2-glyoxylate of formula (III), wherein alk is as previously defined, with an appropriate phenylamine of formula (IV), wherein n is an integer from 0 to 3 and each X is a member selected from the group consisting of hydrogen, loweralkyl, loweralkyloxy and halo, the corresponding α-imino-acetates of formula (II) wherein R is phenyl or substituted phenyl are obtained (II-a). The reaction may be conducted in an anhydrous inert organic solvent, such as, for example, the aromatic hydrocarbons and halocarbons previously described and, preferably, under reflux conditions with azeotropic removal of water formed during the course of the reaction. The presence of a catalytic amount of a strong acid, e.g., an organic acid such as toluenesulfonic acid, methanesulfonic acid and the like or a mineral acid such as $H_2SO_4$, HCl and the like, may be employed to enhance the rate of reaction.

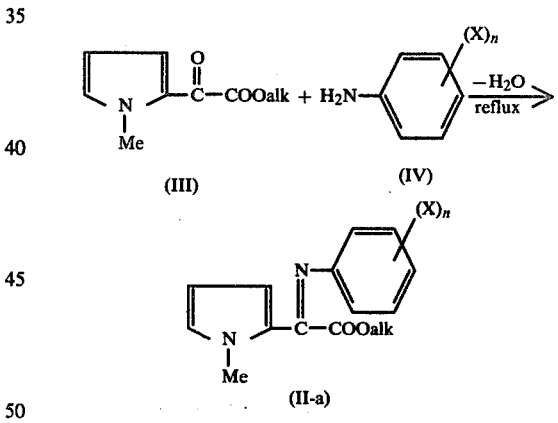

The α-imino-acetates of formula (II) wherein R is loweralkyl or cycloalkyl (II-b) may be prepared by reacting the glyoxylate of formula (III) with a stoichiometric excess of an appropriate alkylamine of formula (V), wherein Y is a member selected from the group consisting of loweralkyl and cycloalkyl, in an aprotic organic solvent under an inert atmosphere, e.g., nitrogen, argon and the like, and in the presence of titanium tetrachloride. At least six molar equivalents of (V) to one molar equivalent of (III) is preferred. Suitable solvents include aromatic hydrocarbons, e.g., benzene, toluene, xylene and the like; ethers, e.g., diethyl ether, dioxane, tetrahydrofuran and the like; and halogenated hydrocarbons, e.g., methylene dichloride, chloroform and the like. The reaction is preferably conducted in the cold, e.g., at temperatures from about $-20°$ C. to about $10°$ C.

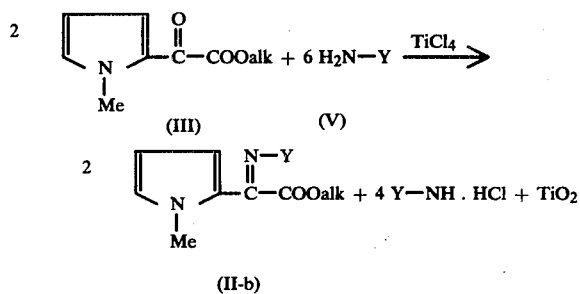

The α-imino-acetates of formula (II) wherein R is hydrogen may be prepared by the interaction of N-methylpyrrole (VI) and loweralkyl cyanoformate (VII) in the presence of hydrogen chloride under Houben Hoesch reaction conditions. In general, dry HCl gas is bubbled through a solution of (VI) and (VII) in an aprotic organic solvent suitable for Houben Hoesch reactions, e.g., ethers, halogenated hydrocarbons, aromatic hydrocarbons, and the like. Alternatively, an ethereal solution of HCl is slowly added to the solution of (VI) and (VII). The resultant loweralkyl α-imino-1-methylpyrrole-2-acetate HCl salt (VIII) is transformed to the corresponding free imino state (II-c) by treatment with at least an equivalent amount of a suitable base, e.g., an alkali metal carbonate or bicarbonate, or a liquid amine which can serve as a halogen acid acceptor such as pyridine, triethylamine and the like.

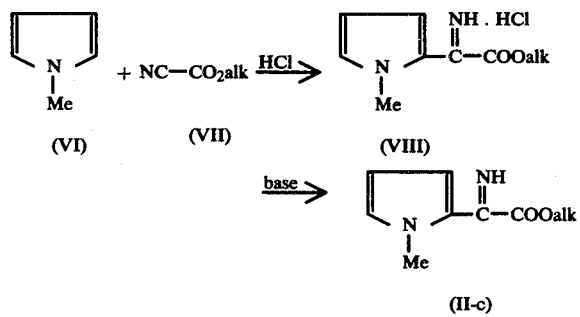

The loweralkyl 1-methylpyrrole-2-glyoxylates of formula (III) may be prepared according to the method described by A. Treibs and F. H. Kreuzer, Ann., 721, 105 (1969). The loweralkyl cyanoformates of formula (VII) may be prepared in accordance with the method described by M. E. Childs and W. P. Weber, J. Org. Chem., 41, 3486 (1976).

The α-imino-acetates of formulas (II-a), (II-b) and (II-c), collectively represented by formula (II), are subsequently reduced to the desired loweralkyl 1-methyl-pyrrole-2-acetates of formula (I) using a divalent sulfur reducing agent as previously described.

EXAMPLE 1

A. Ethyl 1-methylpyrrole-2-acetate: A stream of dry hydrogen chloride is passed at a moderate rate through a solution of 12.5 g of N-methylpyrrole and 16.8 g of ethyl cyanoformate in 125 mls of ethanol-free chloroform at 22° C. for 3½ hours. The reaction mixture is added dropwise with stirring to a 1.5 liter solution of 5% sodium bicarbonate. The chloroform layer is separated, dried over $Na_2SO_4$ and evaporated in vacuo at room temperature to give a brown oil (ethyl α-imino-1-methylpyrrole-2-acetate). The oil is dissolved in 125 ml of ethanol. Hydrogen sulfide is passed through the solution vigorously for 45 mins at 22° C. The mixture is allowed to stand for 16 hrs. The solvent is evaporated in vacuo. The residue is taken up in chloroform. Sulfur is removed by filtration. The chloroform is evaporated in vacuo. The residue is distilled in vacuo to give 15.5 g (60% yield) of oily ethyl 1-methylpyrrole-2-acetate, b.p. 64°–66° C. at 0.06 Torr.

B. The procedure of Example I-A is followed except that an equivalent amount of methyl cyanoformate and n-butyl cyanoformate are substituted for the ethyl cyanoformate used therein to yield, as respective products:
methyl 1-methylpyrrole-2-acetate; and
n-butyl 1-methylpyrrole-2-acetate.

EXAMPLE II

A. Ethyl α-imino-1-methylpyrrole-2-acetate hydrochloride: A stream of dry hydrogen chloride is bubbled slowly into a solution of 2.7 g of ethyl cyanoformate and 2.0 g of N-methylpyrrole in 20 ml of ethanol-free chloroform at 22° C. for 5¾ hrs. The imine hydrochloride is measured by hydrolyzing for 30 mins with water and determining the hydrolysis product, ethyl 1-methylpyrrole-2-glyoxylate, gas chromatographically with internal standard. A 75% yield is measured.

B. Following the procedure above but substituting toluene and tetrahydrofuran for chloroform, yields of 65% and 70%, respectively, are obtained.

EXAMPLE III

Ethyl-1-methylpyrrole-2-acetate: A 28 ml solution of ethereal hydrogen chloride (0.049 mole of HCl) is added dropwise over a 3 hr period to a solution of 2.1 g of N-methylpyrrole and 2.9 g of ethyl cyanoformate in 3 ml ether. The ether supernatant is decanted off, and the precipitate taken up in 11 mls of dry pyridine and the mixture transferred to a pressure bottle. Hydrogen sulfide (13 g) is added to the mixture at −78° C., the bottle sealed, and the mixture is stirred at ambient temperature overnight (about 16 hours). Gas chromatographic analysis with internal standards shows 57% yield of ethyl N-methylpyrrole-2-acetate.

EXAMPLE IV

Ethyl-1-methylpyrrole-2-acetate: Dry hydrogen chloride gas is bubbled slowly into a solution of N-methylpyrrole (5 g) and ethyl cyanoformate (6.72 g) in 50 ml of dry spectral grade chloroform for 3.3 hrs at 25° C. The excess hydrogen chloride and a portion of the chloroform are evaporated off; 50 ml of 2-methoxyethanol is added; and the remaining chloroform evaporated under vacuum. Then 25 ml of dry triethylamine is added and hydrogen sulfide is vigorously bubbled through the solution for 30 min. Gas chromatographic analysis with internal standard shows 50% yield of ethyl 1-methylpyrrole-2-acetate.

EXAMPLE V

Ethyl-1-methylpyrrole-2-acetate: Dry hydrogen chloride is bubbled slowly into a solution of N-methylpyrrole (1 g) and ethyl cyanoformate (1.35 g) in dry spectral grade chloroform (10 ml) for 4 hrs at 25° C. The solution is then added dropwise to 10 ml of triethanolamine with simultaneous introduction of hydrogen sulfide gas bubbled through the solution over a 1.5 hr period. Gas chromatographic analysis with internal standard shows 61% yield of ethyl 1-methylpyrrole-2-acetate.

EXAMPLE VI

Ethyl α-(4-methoxyphenylimino)-1-methylpyrrole-2-acetate: To a solution of 4.0 g ethyl 1-methylpyrrole-2-glyoxylate and 2.96 g p-anisidine in 20 ml toluene is added 24 mg p-toluenesulfonic acid. Heating at reflux for 4 days with water being removed with a Dean-Stark trap is followed by washing successively with aqueous hydrochloric acid, aqueous sodium bicarbonate and brine. After drying, evaporation of the solvent affords a dark solid. Recrystallization from isopropanol gives a 58% yield of ethyl α-(4-methoxyphenylimino)-1-methylpyrrole-2-acetate, m.p. 83°–85° C.

EXAMPLE VII

Ethyl 1-methylpyrrole-2-acetate: sodium ethoxide, 1.14 g, is added to 4.57 g hydrogen sulfide dissolved in 50 ml ethanol. A portion of this solution, 4.12 ml, is added to 0.20 g ethyl α-(4-methoxyphenylimino)-1-methylpyrrole-2-acetate and stirred 2 hrs. Analysis by gas chromatography with an internal standard measures 29% ethyl 1-methylpyrrole-2-acetate.

EXAMPLE VIII

Ethyl α-cyclohexylimino-1-methylpyrrole-2-acetate: To a solution of 25 g ethyl 1-methylpyrrole-2-glyoxylate and 44.5 g cyclohexylamine in 700 ml ether under nitrogen at 0° C. is added 8.8 ml of titanium tetrachloride in 80 ml pentane. After stirring at room temperature overnight, the precipitate is removed by filtration. The filtrate is evaporated and the resulting oil distilled. The fraction collected at 111°–117° C. (5 millitorr) is crystallized from hexane to afford a 15% yield of ethyl α-cyclohexylimino-1-methylpyrrole-2-acetate, m.p. 35°–36° C.

EXAMPLE IX

Ethyl α-phenylimino-1-methylpyrrole-2-acetate: To a solution of 4.0 g ethyl 1-methylpyrrole-2-glyoxylate and 2.23 g aniline in 20 ml toluene is added 30 mg p-toluenesulfonic acid. Heating at reflux for 2 days with water being removed with a Dean-Stark trap is followed by dilution with ether. The precipitate is removed by filtration and the filtrate washed successively with aqueous hydrochloric acid, aqueous sodium bicarbonate and brine. After drying, the solvent is evaporated to afford a residue which is recrystallized twice from isopropanol to give a 43% yield of ethyl α-phenylimino-1-methylpyrrole-2-acetate, m.p. 69°–71° C.

EXAMPLE X

A. Ethyl 1-methylpyrrole-2-acetate: Ten equivalents (0.7 g) of hydrogen sulfide is added to a solution of 0.60 g ethyl α-(4-methoxyphenylimino)-1-methylpyrrole-2-acetate in 38 ml dimethyl sulfoxide at −78° C. in a pressure bottle. The bottle is sealed and the solution is stirred at room temperature for 4 hrs. Excess hydrogen sulfide is vented and the mixture is diluted with chloroform. Analysis by gas chromatography with an internal standard measures 97% ethyl 1-methylpyrrole-2-acetate.

B. Using the above procedure, a solution of ethyl α-phenylimino-1-methylpyrrole-2-acetate in 6.0 ml methanol produces 74% product. Likewise, a solution of ethyl α-cyclohexylimino-1-methylpyrrole-2-acetate in 2.5 ml methanol produces 88% product.

EXAMPLE XI

A. By following the procedure of Example VI, except that an equivalent amount of 4-chloroaniline, 4-ethoxyaniline, 2-bromo-4-ethylaniline, 2,4-dimethoxyaniline, 2,4,6-trimethylaniline and 2,4,6-trichloroaniline are substituted for the p-anisidine used therein, the following respective products are obtained:
ethyl α-(4-chlorophenylimino)-1-methylpyrrole-2-acetate;
ethyl α-(4-ethoxyphenylimino)-1-methylpyrrole-2-acetate;
ethyl α-(2-bromo-4-ethylphenylimino)-1-methylpyrrole-2-acetate;
ethyl α-(2,4-dimethoxyphenylimino)-1-methylpyrrole-2-acetate;
ethyl α-(2,4,6-trimethylphenylimino)-1-methylpyrrole-2-acetate; and
ethyl α(2,4,6-trichlorophenylimino)-1-methylpyrrole-2-acetate.

B. Each of the foregoing α-imino-acetates may be reduced to ethyl 1-methylpyrrole-2-acetate according to the procedure of Example XI-A using H₂S as the reducing agent.

EXAMPLE XII

A. The procedure of Example VIII is repeated except that an equivalent quantity of n-butylamine and cyclopentylamine is substituted for the cyclohexylamine use therein to yield, as respective products:
ethyl α-n-butylimino-1-methylpyrrole-2-acetate; and
ethyl α-cyclopentylimino-1-methylpyrrole-2-acetate.

B. Reduction of each of the foregoing α-imino-acetates to ethyl 1-methylpyrrole-2-acetate with H₂S as the reducing agent may be carried out according to the procedure of Example XI-a.

We claim:

1. A process of preparing a loweralkyl 1-methylpyrrole-2-acetate which comprises reducing a loweralkyl α-imino-1-methylpyrrole-2-acetate having the formula:

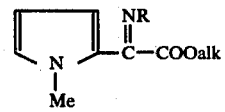

wherein:
alk is loweralkyl; and
R is a member selected from the group consisting of hydrogen, loweralkyl, cyclopentyl, cyclohexyl, phenyl and phenyl substituted with from one to three substituents each selected from the group consisting of loweralkyl, loweralkyloxy and halo;
by the action of a divalent sulfur reducing agent selected from the group consisting of hydrogen sulfide, an alkali metal hydrogen sulfide, sodium polysulfide and ammonium polysulfide.

2. The process of claim 1 wherein said reducing agent is a member selected from the group consisting of hydrogen sulfide and sodium hydrogen sulfide.

3. A process of preparing ethyl 1-methylpyrrole-2-acetate which comprises reducing an ethyl α-imino-1-methylpyrrole-2-acetate having the formula:

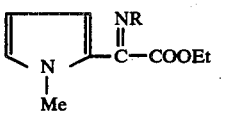

wherein: R is a member selected from the group consisting of hydrogen, loweralkyl, cyclopentyl, cyclohexyl, phenyl and phenyl substituted with from one to three substituents each selected from the group consisting of loweralkyl, loweralkyloxy and halo;
by the action of hydrogen sulfide as the reducing agent.

4. A process of preparing ethyl 1-methylpyrrole-2-acetate which comprises reducing ethyl α-imino-1-methylpyrrole-2-acetate by the action of hydrogen sulfide as the reducing agent.

5. A process of preparing ethyl 1-methylpyrrole-2-acetate which comprised reducing ethyl α-(4-methoxyphenylimino)-1-methylpyrrole-2-acetate by the action of sodium hydrogen sulfide as the reducing agent.

6. A process of preparing ethyl 1-methylpyrrole-2-acetate which comprises reducing ethyl α-(4-methoxyphenylimino)-1-methylpyrrole-2-acetate by the action of hydrogen sulfide as the reducing agent.

7. A process of preparing ethyl 1-methylpyrrole-2-acetate which comprises reducing ethyl α-cyclohexylimino-1-methylpyrrole-2-acetate by the action of hydrogen sulfide as the reducing agent.

8. A process of preparing ethyl 1-methylpyrrole-2-acetate which comprises reducing ethyl α-phenylimino-1-methylpyrrole-2-acetate by the action of hydrogen sulfide as the reducing agent.

9. A process of preparing a loweralkyl 1-methylpyrrole-2-acetate which comprises reducing a loweralkyl α-imino-1-methylpyrrole-2-acetate having the formula:

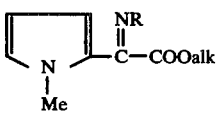

wherein:
alk is loweralkyl; and
R is a member selected from the group consisting of hydrogen, loweralkyl, cyclopentyl, cyclohexyl, phenyl and phenyl substituted with from one to three substituents each selected from the group consisting of loweralkyl, loweralkyloxy and halo;
by the action of a divalent sulfur reducing agent selected from the group consisting of hydrogen sulfide, an alkali metal hydrogen sulfide, sodium polysulfide and ammonium polysulfide at reaction temperatures of from about −20° to about 50° C. and atmospheric to about 60 p.s.i. pressure.

10. The process of claim 9 wherein said reducing agent is a member selected from the group consisting of hydrogen sulfide and sodium hydrogen sulfide.

11. A process of preparing ethyl 1-methylpyrrole-2-acetate which comprises reducing an ethyl α-imino-1-methylpyrrole-2-acetate having the formula:

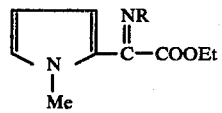

wherein: R is a member selected from the group consisting of hydrogen, loweralkyl, cyclopentyl, cyclohexyl, phenyl and phenyl substituted with from one to three substituents each selected from the group consisting of loweralkyl, loweralkyloxy and halo;
by the action of hydrogen sulfide at reaction temperatures of from about −20° to about 50° C. and atmospheric to about 60 p.s.i. pressure.

12. A process of preparing ethyl 1-methylpyrrole-2-acetate which comprises reducing ethyl α-imino-1-methylpyrrole-2-acetate by the action of hydrogen sulfide as the reducing agent at reaction temperatures of from about −20° to about 50° C. and atmospheric to about 60 p.s.i. pressure.

13. A process of preparing ethyl 1-methylpyrrole-2-acetate which comprises reducing ethyl α-(4-methoxyphenylimino)-1-methylpyrrole-2-acetate by the action of sodium hydrogen sulfide as the reducing agent at reaction temperatures of from about −20° to about 50° C. and atmospheric to about 60 p.s.i. pressure.

14. A process of preparing ethyl 1-methylpyrrole-2-acetate which comprises reducing ethyl α-(4-methoxyphenylimino)-1-methylpyrrole-2-acetate by the action of hydrogen sulfide as the reducing agent at reaction temperatures of from about −20° to about 50° C. and atmospheric to about 60 p.s.i. pressure.

15. A process of preparing ethyl 1-methylpyrrole-2-acetate which comprises reducing ethyl α-cyclohexylimino-1-methylpyrrole-2-acetate by the action of hydrogen sulfide as the reducing agent at reaction temperatures of from about −20° to about 50° C. and atmospheric to about 60 p.s.i. pressure.

16. A process of preparing ethyl 1-methylpyrrole-2-acetate which comrpises reducing α-phenylimino-1-methylpyrrole-2-acetate by the action of hydrogen sulfide as the reducing agent at reaction temperatures of from about −20° to about 50° C. and atmospheric to about 60 p.s.i. pressure.

* * * * *